US008768452B2

(12) United States Patent
Gerber

(10) Patent No.: US 8,768,452 B2
(45) Date of Patent: *Jul. 1, 2014

(54) IMPLANTABLE NEUROSTIMULATOR SUPPORTING TRIAL AND CHRONIC MODES

(75) Inventor: Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 699 days.

This patent is subject to a terminal disclaimer.

(21) Appl. No.: 11/116,932

(22) Filed: Apr. 28, 2005

(65) Prior Publication Data

US 2006/0195152 A1 Aug. 31, 2006

Related U.S. Application Data

(60) Provisional application No. 60/655,557, filed on Feb. 23, 2005.

(51) Int. Cl.
*A61N 1/00* (2006.01)

(52) U.S. Cl.
USPC .................................. 607/2; 607/59

(58) Field of Classification Search
USPC ...................................... 607/2, 59
See application file for complete search history.

(56) References Cited

U.S. PATENT DOCUMENTS

| | | | | |
|---|---|---|---|---|
| 5,836,989 | A * | 11/1998 | Shelton | 607/27 |
| 6,169,924 | B1 * | 1/2001 | Meloy et al. | 607/39 |
| 6,687,538 | B1 | 2/2004 | Hrdlicka et al. | |
| 7,065,412 | B2 * | 6/2006 | Swoyer et al. | 607/117 |
| 7,146,223 | B1 * | 12/2006 | King | 607/117 |
| 2002/0143376 | A1 | 10/2002 | Chinn et al. | |
| 2003/0199948 | A1 * | 10/2003 | Kokones et al. | 607/117 |
| 2004/0215287 | A1 | 10/2004 | Swoyer et al. | |
| 2006/0190048 | A1 | 8/2006 | Gerber | |

FOREIGN PATENT DOCUMENTS

WO WO 98/29160 7/1998

OTHER PUBLICATIONS

International Search Report for PCT Application Serial No. PCT/US2006/006149 dated Jun. 1, 2006, (4 pgs.).
International Preliminary Report on Patentability for PCT Application Serial No. PCT/US2006/006149 dated Jun. 12, 2007, (10 pgs.).
Office Action dated May 3, 2007 for Application Serial No. 11/116,953, filed Apr. 28, 2005 (7 pgs.).

(Continued)

*Primary Examiner* — Eric D. Bertram
(74) *Attorney, Agent, or Firm* — Shumaker & Sieffert, P.A.

(57) ABSTRACT

The disclosure is directed to a chronic implantable neurostimulator that supports trial and chronic modes of operation. The implantable neurostimulator can alternatively include one or more sensors that may or may not function differently in trial and chronic modes. In particular, the device is designed to be used as both a trial neurostimulator and a permanent, or chronic, neurostimulator. A trial neurostimulation period is generally desired to evaluate the efficacy of the therapy. A percutaneous or implantable trial neurostimulator is used for the trial neurostimulation period. In most cases, the trial period is successful, in which case the trial stimulator is explanted and replaced with a permanent, i.e., "chronic," implantable stimulator. In accordance with the disclosure, an implantable neurostimulator supports both trial neurostimulation and chronic neurostimulation in the event trial stimulation is successful. In this manner, the additional surgery ordinarily required for replacement of the trial stimulator can be avoided. Instead, the implanted neurostimulation device remains implanted and is reconfigured to transition from trial stimulation to chronic stimulation.

26 Claims, 7 Drawing Sheets

(56) References Cited

OTHER PUBLICATIONS

Responsive Amendment for U.S. Appl. No. 11/116,953 dated Aug. 3, 2007 (14 pgs.).
Restriction Requirement for U.S. Appl. No. 11/116,953 dated Oct. 26, 2007 (6 pgs.).
Response to Restriction Requirement for U.S. Appl. No. 11/116,953 dated Nov. 21, 2007 (1 pgs.).
Office Action for U.S. Appl. No. 11/116,953 dated Feb. 20, 2008 (9 pgs.).
Responsive Amendment for U.S. Appl. No. 11/116,953 dated May 20, 2008 (15 pgs.).
Office Action dated Jun. 11, 2008 for U.S. Appl. No. 11/116,953 (10 pgs.).
Response for U.S. Appl. No. 11/116,953 dated Oct. 10, 2008 (8 pgs.).
Office Action dated Jan. 7, 2009 for U.S. Appl. No. 11/116,953 (7 pgs.).
Responsive Amendment dated May 7, 2009 for U.S. Appl. No. 11/115,953 (12 pgs.).
Office Action dated Feb. 24, 2010 for U.S. Appl. No. 11/116,953 (9 pgs.).
Responsive Amendment dated Jun. 24, 2010 for U.S. Appl. No. 11/116,953 (15 pgs.).
Office Action dated Sep. 20, 2010 for U.S. Appl. No. 11/116,953 (10 pgs.).
Notice of Appeal dated Dec. 20, 2010 for U.S. Appl. No. 11/116,953 (1 pg.).
Decision on Appeal dated Dec. 16, 2013, from U.S. Appl. No. 11/116,953, 12 pages.
Office Action from U.S. Appl. No. 13/968,290, dated Jan. 17, 2014, 13 pp.
Amendment in response to the Decision on Appeal from the Patent Trial and Appeal Board from U.S. Appl. No. 11/116,953, filed Feb. 14, 2014, 10 pp.
Response to Office Action dated Jan. 17, 2014, from U.S. Appl. No. 13/968,290, filed Apr. 17, 2014, 14 pp.
Notice of Allowance from U.S. Appl. No. 11/116,953, dated Feb. 25, 2014, 24 pp.

\* cited by examiner

IMPLANTABLE NEUROSTIMULATOR SUPPORTING TRIAL AND CHRONIC MODES

PRIORITY OF INVENTION

This invention claims priority from U.S. Provisional Application No. 60/655,557, filed on Feb. 23, 2005, entitled "IMPLANTABLE NEUROSTIMULATOR SUPPORTING TRIAL AND CHRONIC MODES", the disclosure of which is incorporated in its entirety by reference herein

TECHNICAL FIELD

The invention relates generally to implantable medical devices and, more particularly, to devices for delivery of neurostimulation therapy.

BACKGROUND

A variety of pelvic floor disorders such as urinary control disorders, fecal control disorders, interstitial cystitis, sexual dysfunction and pelvic pain are influenced by the sacral nerves. In particular, the organs involved in various bodily functions receive much of their control via the second, third, and fourth sacral nerves, commonly referred to as S2, S3, and S4, respectively. The sacrum, in general, is a large, triangular bone situated at the lower part of the vertebral column, and at the upper and back part of the pelvic cavity. The spinal canal runs throughout the sacrum. The sacral nerves pass through the sacrum via the anterior and posterior sacral foramina. These organs are also innervated via other nerves, such as the pudendal nerve.

Electrical stimulation of the sacral nerves, pudendal nerves, and other nerves of the pelvic floor has been found to offer relief for many pelvic floor disorders. For example, medical leads having discrete electrodes are implanted on and near the sacral nerves. An implantable pulse generator drives the electrodes with an electrical signal to stimulate the sacral nerves, and thereby restore or control bodily functions affected by pelvic floor disorders. Several techniques of electrical stimulation may be used, including stimulation of nerve bundles within the sacrum.

Chronic implantation of a pulse generator and lead for sacral nerve stimulation is typically preceded by a trial period. The trial period ordinarily has a prescribed maximum duration, but sometimes is exceeded by the patient or the physician.

During the trial period, a clinician evaluates the efficacy of sacral nerve stimulation in alleviating the patient's disorder to determine whether the patient is a good candidate for chronic implantation.

The trial period ordinarily involves implantation of a temporary or chronic lead, and percutaneous connection of the lead to an external trial stimulator. Often, connection of the lead to the trial stimulator involves extensive subcutaneous tunneling of the lead to a percutaneous exit site. In addition, the percutaneous connection presents a significant risk of infection. To reduce infection risk, the lead is ordinarily tunneled away from the site selected for chronic implant, requiring added time and effort by the surgeon.

Neurostimulation efficacy and patient response can also be determined using a fully implantable neurostimulator specifically designed to operate during a brief trial period. Implantation of a neurostimulator with a limited power source or timed termination feature is disclosed in U.S. Publication 20040215287, to Swoyer et al., the entire content of which is incorporated herein by reference. The implantable trial neurostimulator described in the Swoyer et al. application is removed after the trial period and replaced with a chronic neurostimulator if the patient responds positively to the trial therapy.

SUMMARY

The invention is directed to a chronic implantable neurostimulator that supports both trial and chronic modes of operation. In particular, the neurostimulator is designed to be used as both a trial neurostimulator and a permanent, or chronic, neurostimulator.

A trial neurostimulation period is generally desired to evaluate the efficacy of the therapy. A percutaneous or implantable trial neurostimulator is used for the trial neurostimulation period. In most cases, the trial period is successful, in which case the trial stimulator is explanted and replaced with a permanent, i.e., "chronic," implantable stimulator.

In accordance with the invention, an implantable neurostimulator supports both trial neurostimulation and chronic neurostimulation. In the event trial stimulation is successful, the need for explant and replacement is eliminated. In this manner, using the same neurostimulator for trial and chronic stimulation, the additional surgery ordinarily required for replacement of the trial stimulator can be avoided. Instead, the implanted neurostimulation device remains implanted and is reconfigured to transition from trial stimulation to chronic stimulation.

The implantable neurostimulator invokes a trial mode of neurostimulation in which the device is partially or fully operable, but only operates for a trial period of finite duration. Upon expiration of the trial period, the implantable neurostimulator stops operating, unless it receives additional authorization to either extend the trial mode or enter a chronic mode of operation.

The trial mode enables the clinician to evaluate the efficacy of the neurostimulation device in terms of treating a disorder and avoiding undesirable side effects. Upon initial implantation, the trial period commences and continues until the trial period has lapsed. The trial period may be tracked by the implanted neurostimulation device or an external patient programmer. Hence, the implanted neurostimulation device may disable itself unilaterally, in response to a disable command from an external programmer, or in the absence of a periodic authorization command from an external programmer.

Upon completion of the trial period, a clinician may upload patient information gathered during the trial period, interview the patient, and/or take other steps helpful in evaluating the efficacy of the therapy. If the therapy has been successful, as it most commonly is, the patient may continue to use the implanted neurostimulator and its associated implanted lead without the need for another surgical procedure. In particular, the clinician may authorize continued use of the implanted medical device in a chronic mode of operation.

The authorization to continue use in a chronic mode may be provided in a variety of ways. For example, the clinician may simply download an authorization code to the implanted neurostimulator, which authorizes the neurostimulator to continue operation. The authorization code may unlock the neurostimulator from a frozen state, or unlock parameters or programs necessary for chronic operation. Alternatively, the clinician may reprogram the implanted neurostimulation device by downloading new parameters or programs that govern the chronic mode. In general, the chronic mode is intended for relatively long term stimulation therapy over an extended, indefinite time period. However, it may be possible for a patient to discontinue the therapy at any time using a patient programmer.

In other embodiments, instead of or, in addition to, authorizing transition from the trial mode to the chronic mode, authorization may serve to unlock additional features of the implanted stimulator. As examples, a clinician or administrator, or a manufacturer of the implanted stimulator, may provide an authorization to activate features such as a voiding diary, different algorithms, different stimulation patterns and the like. The authorization could be provided to any element within the neurostimulation system, such as a physician programmer, patient programmer or the implanted stimulator.

In one embodiment, the invention provides a method comprising implanting a neurostimulator in a patient, operating the neurostimulator in a trial mode to evaluate efficacy of the neurostimulator, and operating the neurostimulator in a chronic mode if the trial mode indicates an acceptable level of efficacy. The neurostimulator may be explanted from the patient if the trial mode does not indicate the acceptable level of efficacy. The trial mode extends over a relatively short trial period, such as less than six months, less than one month, or less than one week. The chronic mode may extend for more than six months, and preferably more than one year.

In another embodiment, the invention provides an implantable neurostimulator comprising a pulse generator, a memory storing a trial mode program and a chronic mode program, and a processor that controls the pulse generator to apply stimulation pulses according to either the trial mode program or the chronic mode program.

One embodiment of the invention also incorporates one or more sensors. In some embodiments, the one or more sensor can gather different information, gather information at different time intervals, or some combination thereof during trial mode and chronic mode. In one embodiment, the one or more sensor gathers information more frequently during the trial mode than it does during the chronic mode.

The invention may provide one or more advantages. For example, an implantable neurostimulator that supports both trial and chronic modes of operation can be used in a trial period without the need for percutaneous extensions, and does not require explantation for replacement by a chronic stimulator if the trial period is successful. In this manner, the surgeon benefits from reduced surgical effort and time, while the patient benefits from reduced surgical trauma, recovery and infection risks. In some case, the implantable neurostimulator will be explanted when the trial period is not successful. However, it is expected that explantation will be necessary in only a minority of cases, and is generally outweighed by the advantage of avoiding explantation for those patients for whom the trial period was successful. As a further advantage, the time between the end of the trial period and the beginning of chronic therapy can be reduced because there is no need for explantation and replacement of the trial stimulator.

The details of one or more embodiments of the invention are set forth in the accompanying drawings and the description below. Other features, objects, and advantages of the invention will be apparent from the description and drawings, and from the claims.

DETAILED DESCRIPTION

The invention, as described herein, is directed to an implantable neurostimulator for delivering neurostimulation therapy to a patient in both a trial mode and a chronic mode. In the trial mode, the neurostimulator delivers therapy that permits a clinician and patient to evaluate the efficacy of the therapy. The trial period may run for a relatively short period of time, such as several hours, days, weeks, or months. If the trial mode indicates desirable efficacy, the neurostimulator enters a chronic mode in which the neurostimulator delivers neurostimulation on a permanent basis over an extended period of time, such as several months or years.

Although the invention may be described in the context of neurostimulation for pelvic floor disorders, for purposes of illustration, the invention may be readily applicable to other forms of neurostimulation or other neurostimulation applications in which a trial period is desirable, including but not limited to spinal cord stimulation for relief of chronic, intractable pain, gastric stimulation for treatment of gastric mobility disorders or obesity, and stimulation for the treatment of sexual dysfunction. Sacral nerve stimulation will be described herein for purposes of illustration. However, the invention may be applied to applications involving stimulation of other nerves, such as pudendal nerves, perineal nerves, the spinal cord, the stomach, or other areas of the nervous system.

Figure 1:
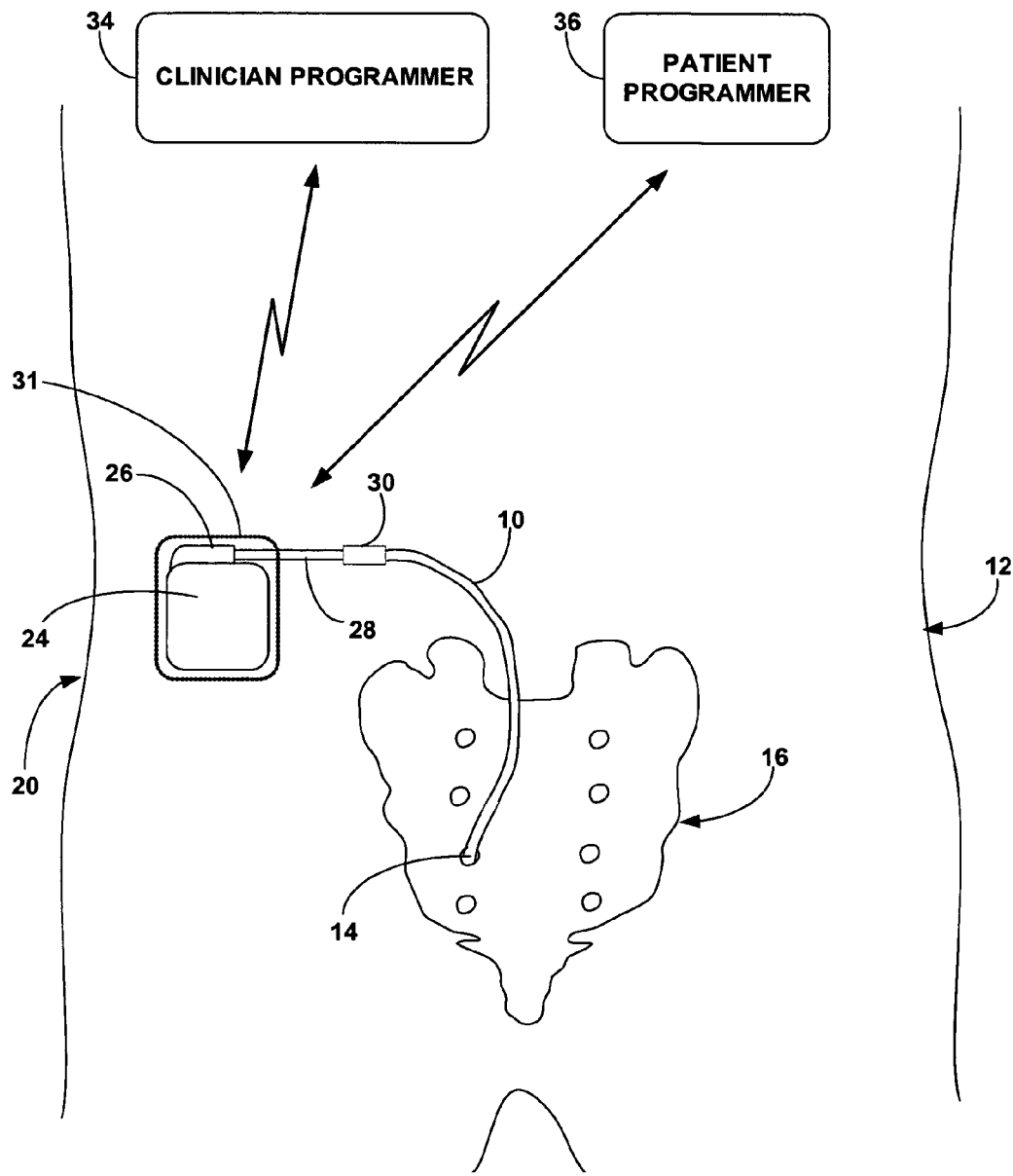
FIG. 1 is a diagram illustrating an implantable neurostimulation system designed to support both a trial mode and a chronic mode of operation.

FIG. 1 is a diagram illustrating an implantable neurostimulation system 20 for sacral nerve stimulation via at least one lead 10. Neurostimulation system 20 includes an implantable neurostimulator 24 that supports both a trial stimulation mode and a chronic stimulation mode. Neurostimulation system 20 delivers neurostimulation to the sacral nerves or other regions of the nervous system known to influence pelvic floor disorders, urinary control disorders, fecal control disorders, interstitial cystitis, sexual dysfunction, pelvic pain, or some combination thereof.

Neurostimulator 24 includes an implantable pulse generator, and delivers neurostimulation therapy to patient 12 in the form of electrical pulses generated by the implantable pulse generator. In the example of FIG. 1, neurostimulator 24 is implanted in the upper left buttock of patient 12, but may be implanted at other locations. A proximal end of stimulation lead 10 is coupled to a connector block 26 associated with neurostimulator 24. As shown in FIG. 1, lead 10 may be coupled to connector block 26 via a lead extension 28 and connector 30. Neurostimulator 24 may be implanted within a subcutaneous pocket 31 that serves as the implant site. Subcutaneous pocket 31 is formed by a surgical procedure.

Lead 10 carries one or more stimulation electrodes to permit delivery of electrical stimulation to sacral nerves. For example, implantable neurostimulation system 20 may stimulate organs involved in urinary, fecal or sexual function via C-fibers or sacral nerves at the second, third, and fourth sacral nerve positions, commonly referred to as S2, S3, and S4, respectively. Also, in some embodiments, lead 10 may carry one or more sense electrodes to permit neurostimulation device 24 to sense electrical signals within sacrum 16.

Accordingly, lead 10 includes an outer lead body that contains one or more conductors to electrically couple the electrodes to terminals within connector block 26. In some embodiments, trial neurostimulator 24 may be coupled to two or more leads deployed at different positions relative to the spinal cord or sacral nerves, for example.

Implantable neurostimulator 24 eliminates the need for a percutaneous connection for trial stimulation, reducing the risk of infection and affording greater convenience and comfort to the patient. Moreover, the absence of a percutaneous connection makes the neurostimulator easier to tolerate, and presents a reduced infection risk, permitting trial periods to run for extended period of times. The trial period may run for days, weeks or even months, in view of heightened patient tolerance. As examples, the trial period may be less than one month or, in some cases, less than six months.

Neurostimulator 24 supports both trial stimulation and chronic stimulation. Consequently, neurostimulator 24 offers the convenience of fewer surgical procedures for patients by enabling both a trial period and chronic operation without the need to remove a trial neurostimulator and replace it with a chronic stimulator after effective trial therapy.

In the trial mode, neurostimulator 24 delivers either a full set of stimulation parameters or a limited set of stimulation parameters specified by a clinician. The patient may be permitted to adjust stimulation parameters, such as amplitude, pulse width and pulse rate, i.e., frequency, during the trial mode. Alternatively, the clinician may specify a set of fixed stimulation parameters or a limited range of adjustment.

In the chronic mode, neurostimulator 24 may deliver a full set of stimulation parameters, and may permit a full range of adjustment by patient 12, subject to limits specified by the clinician. In addition, neurostimulator 24 may accept new parameters, adjusted parameters, or new programs containing parameter sets, via a physician programmer.

In one embodiment of the invention, a device includes at least one sensor. The one or more sensor may provide a variety of information indicative of the level of efficacy achieved by the neurostimulation therapy delivered by neurostimulator. The information may be any information relating to the function of the bladder, or any other segment of the patient's urinary tract, in storing releasing and passing urine. For example, the sensor may monitor parameters such as bladder pressure, bladder contractile force, urinary sphincter pressure, urine flow rate, urine flow pressure, voiding amount, and the like.

Other examples of sensed information include urine flow velocity, urine or bladder temperature, impedance, urinary pH, or chemical constituency of the urine. Any of such information may reveal the effect of the neurostimulation therapy on the physiological function of the bladder, the urethra, or the urinary sphincter. For example, if the sensor indicates excessive pressure, excessive contractile force, or involuntary urine flow (i.e., leakage) in response to a set of stimulation parameters, the information will be gathered by the one or more sensors.

In still other embodiments, the one or more sensors may be implanted within a patient to sense a physiological state of the patient. For example, a sensor may be deployed to sense cardiac activity, respiratory activity, electromyographic activity, or the like, as an indication of patient activity level. Such activity level information, in conjunction with other information, may be useful in determining the efficacy of the stimulation parameters. Other types of sensors may detect a posture or activity level of the patient. For example, an accelerometer may detect an elevated activity level, e.g., during exercise, while other sensors may detect whether the patient is sitting, standing or lying down. In addition, some of the information obtained by such sensors, such as respiration activity, may be analyzed to determine, e.g., whether the patient is sleeping.

In an embodiment including one or more sensors, the function of the one or more sensors can be different during the trial mode and the chronic mode. In one embodiment, the one or more sensors gathers information more frequently in the trial mode than it does in the chronic mode. In one embodiment, for example, the one or more sensors gathers information on an hourly or daily basis in the trial mode, and on a weekly basis in the chronic mode. In another embodiment, at one or more sensors gathers information in response to every voiding event, for example, that is indicated by the patient, and in the chronic mode, information is gathered only in response to every fifth, tenth, or twentieth (for example) voiding event.

In another embodiment including one or more sensors, the information that is gathered during the trial mode includes more physiological parameters than that gathered during the chronic mode. In yet another embodiment including one or more sensors, both the information that is gathered, and the frequency upon which it is gathered is different in the trial mode and the chronic mode. An example of such an embodiment would be a device where more parameters are gathered more often during the trial mode than in the chronic mode.

The one or more sensors, if included in an embodiment of the invention, can carry sufficient battery resources, a rechargeable battery, or an inductive power interface that can permit extended operation. The sensor(s) may be implanted by minimally invasive, endoscopic techniques for example. In some embodiments, the sensor(s) transmits sensed information continuously or periodically to the neurostimulator or the patient programmer. In this case, the sensor(s) can monitor physiological conditions continuously or periodically. Alternatively, the neurostimulator or patient programmer may trigger activation of the sensor(s) to capture information at desired intervals. In some cases, triggered activation may occur when the patient enters information into the patient programmer to indicate a voiding event, for example. Triggered activation of the sensor(s) may be useful in conserving battery life, if applicable, of the sensor(s) or neurostimulator. In one embodiment, multiple sensors may be provided and dedicated to different parameters or different locations within the urinary tract.

In one embodiment of the invention, the sensor(s) can be programmed to gather information at a particular frequency (either the same or different in both the trial and chronic mode), and be configured to gather information when prompted by the patient programmer or the physician programmer. In another embodiment, the sensor(s) are programmed to gather information at a particular frequency during the trial mode and are programmed to be activated when prompted by the patient programmer or physician programmer during the chronic mode. In yet another embodiment, the sensor(s) are programmed to gather information at particular frequencies during the trial and chronic mode (either the same frequency or different frequencies) and can also be activated when prompted by the patient programmer or physician programmer during both the trial mode and the chronic mode.

Rather than immediately transmitting the information to the neurostimulator or the patient programmer, the sensor(s) may initially store the information internally for subsequent wireless transmission. Hence, in some embodiments, the information may be stored within the sensor(s), and later transmitted to the neurostimulator or the patient programmer. In this case, the neurostimulator or the patient programmer may interrogate the sensor(s) to obtain the stored information.

In one embodiment, the sensor(s) can include a sensor processor, a sensing element, memory, wireless telemetry interface, and a power source. The sensor(s) also may include an internal clock to track date and time of voiding events. The sensor(s) may have a capsule-like shape, and may be placed within the bladder or the urethra by endoscopic introduction via the urethra, or by hypodermic injection using a hypodermic needle. Alternatively, the sensor(s) may be surgically implanted. In the case of minimally invasive endoscopic introduction, the sensor(s) may be constructed in a manner similar to the sensors described in U.S. patent application Ser. No. 10/978,233, to Martin Gerber, filed Oct. 29, 2004, and entitled "Wireless Urinary Voiding Diary System," which claims the benefit of U.S. provisional application no. 60/589,442, filed Jul. 20, 2004; or U.S. patent application Ser. No. 10/833,776, to Mark Christopherson and Warren Starkebaum, filed Apr. 28, 2004, entitled "Implantable Urinary Tract Monitor," the entire content of each of which is incorporated herein by reference.

The sensing element may be selected for any of a variety of urodynamic testing applications, and may include appropriate signal processing circuitry such as amplifier, filter, driver, and analog-to-digital conversion circuitry for presentation of sensed information to sensor processor. For urodynamic testing, sensing element may take the form of a pressure, flow, velocity, volume, temperature, impedance, or contractile force sensor. For pressure measurements, for example, sensing element may include one or more diaphragm sensors, strain gauge sensors, capacitive sensors, piezoelectric sensors, or other sensors used in conventional catheter-based urodynamic testing to sense pressure. As a further example, for bladder emptying, sensing element may include a conductive sensor to sense the presence of urine within the lower region of the bladder.

For flow measurements, sensing element may comprise a pulsed Doppler ultrasonic sensor, or a laser Doppler flow sensor. Doppler shifting of the frequency of the reflected energy indicates the velocity of the fluid flow passing over a surface of sensing element. Consequently, in some embodiments, the sensor(s) may include circuitry, such as a quadrature phase detector, in order to enable the monitor to distinguish the direction of the flow of fluid in addition to its velocity.

As a further example, sensing element may include any one or more thermal-convection velocity sensors. A thermal-convection velocity sensor may include a heating element upstream of a thermistor to heat urine within the urethra such that flow rate may be measured according to the temperature of the heated fluid when it arrives at the thermistor. In other embodiments, flow rate may be determined from the output of a concentration or temperature sensor using Fick's techniques.

In some embodiments, the sensing element may include multiple sensors of a given type, as well as multiple types of sensors, e.g., pressure, flow, bladder emptying, or the like. Accordingly, the information obtained by the sensor(s) may then include different types of physiological parameters associated with a voiding event. Alternatively, multiple the sensor(s) may be deployed within the bladder or the urethra. In this case, each of the sensor(s) may be configured with a different type or set of sensing elements to collect a variety of different urodynamic parameters during a voiding event.

In some other embodiments, the sensing element may be chosen to sense a physiological state, such as an activity type, activity level, or posture of the patient. For example, the sensing element can include an accelerometer to detect an elevated activity level, or a decreased activity level.

As further shown in FIG. 1, implantable neurostimulation system 20 also may include a clinician programmer 34 and a patient programmer 36. Clinician programmer 34 may be a handheld computing device that permits a clinician to program neurostimulation therapy for patient 12, e.g., using input keys and a display. For example, using clinician programmer 34, the clinician may specify neurostimulation parameters for use in delivery of neurostimulation therapy.

Clinician programmer 34 supports radio frequency telemetry with neurostimulator 24 to download neurostimulation parameters and, optionally, upload operational or physiological data stored by neurostimulator 24. In this manner, the clinician may periodically interrogate neurostimulator 24 to evaluate efficacy and, if necessary, modify the stimulation parameters. Once the trial period has concluded and has been deemed effective, programmer 34 may have the ability to renew the operational "subscription" of neurostimulator 24 with neurostimulation parameters for chronic stimulation therapy.

Like clinician programmer 34, patient programmer 36 may be a handheld computing device. Patient programmer 36 may also include a display and input keys to allow patient 12 to interact with patient programmer 36 and implantable neurostimulator 24. In this manner, patient programmer 36 provides patient 12 with an interface for control of neurostimulation therapy by neurostimulator 24.

For example, patient 12 may use patient programmer 36 to start, stop or adjust neurostimulation therapy during the trial or chronic mode. In particular, patient programmer 36 may permit patient 12 to adjust stimulation parameters such as duration, amplitude, pulse width and pulse rate within an adjustment range specified by the clinician via clinician programmer 34. In one embodiment of the invention, different options may be provided to the patient during the trial period and the chronic period.

Neurostimulator 24, clinician programmer 34 and patient programmer 36 may communicate via wireless communication, as shown in FIG. 1. Clinician programmer 34 and patient programmer 36 may, for example, communicate via wireless communication with neurostimulator 12 using RF telemetry techniques known in the art. Clinician programmer 34 and patient programmer 36 also may communicate with each other using any of a variety of local wireless communication techniques, such as RF communication according to the 802.11 or Bluetooth specification sets, or other standard or proprietary telemetry protocols.

The trial mode may be initiated by an enable signal transmitted by neurostimulator 24 from clinician programmer 34 or patient programmer 36. Likewise, the trial period may be terminated by a disable command transmitted by clinician programmer 34 or patient programmer 36, e.g., in response to a physician or patient command or upon expiration of a trial period timer.

Alternatively, the trial mode may be operative only so long as neurostimulator 24 continues to receive a periodic enable signal. In this case, if the enable signal is not received within a scheduled interval, neurostimulator 24 disables the trial mode. As a further alternative, once enabled, neurostimulator 24 may track the progress of the trial period using an internal clock or clock derived from an external source, and unilaterally disable the trial mode when the trial period has lapsed.

Upon disablement, neurostimulator 24 may remain idle until it is explanted, in the case of an unsuccessful trial, or until a clinician transmits an authorization command via the clinician programmer 34 or patient programmer 36 to enter the chronic mode, in the case of a successful trial. In the chronic mode, neurostimulator 24 is reactivated and enabled for continued delivery of neurostimulation therapy. In this case, neurostimulator 24 may receive simply the authorization command to invoke a set of parameters or a program stored in the neurostimulator to support the chronic mode. Alternatively, neurostimulator 24 may receive a new parameter or program via the clinician programmer 34 or patient programmer 36, or be entirely reprogrammed. In each case, there is no need for another surgical procedure. Instead, the provisioning of neurostimulator 24 is accomplished by wireless telemetry.

Figure 2:
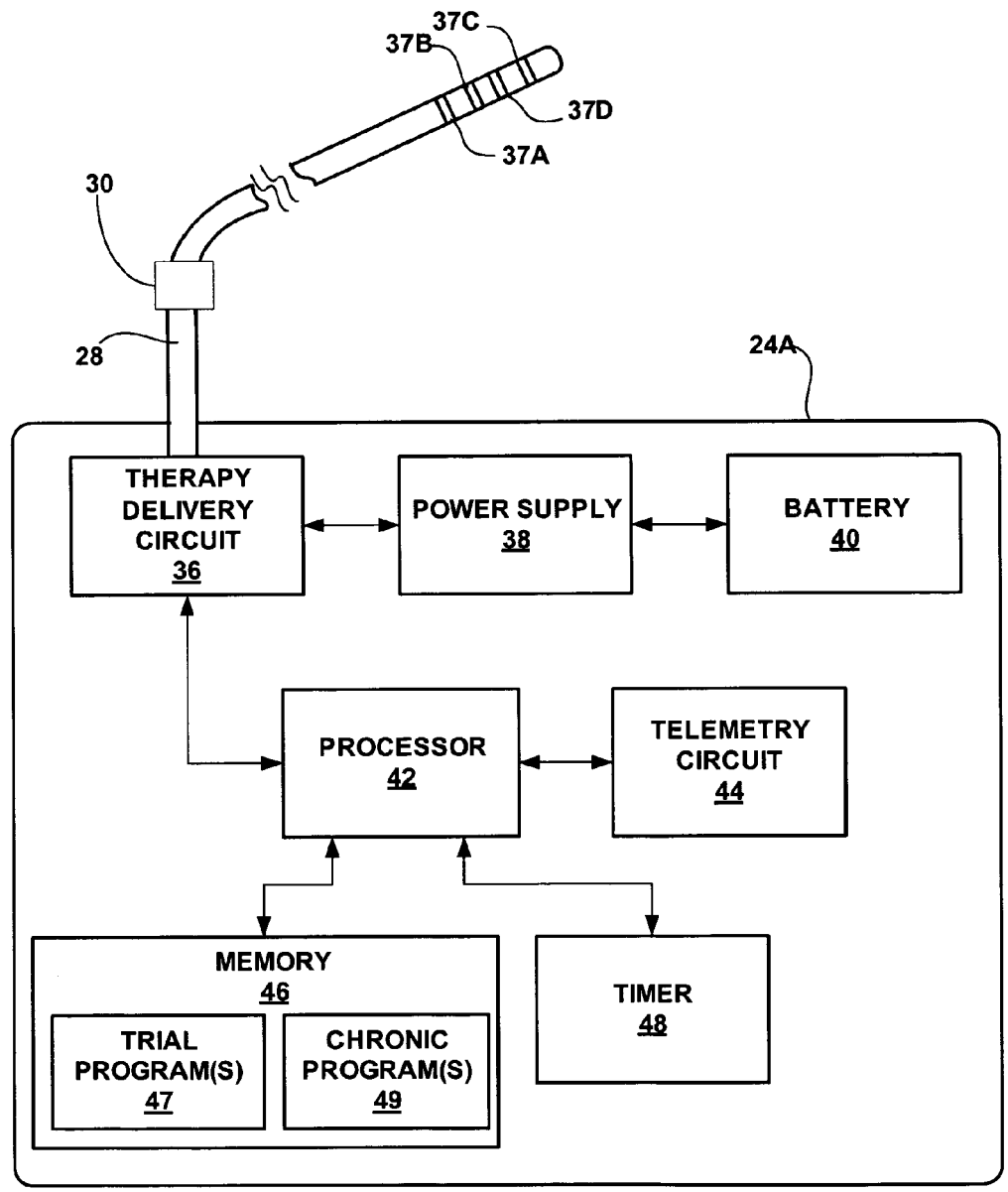
FIG. 2 is a block diagram illustrating various components of an implantable neurostimulator.

FIG. 2 is a block diagram illustrating various components of an implantable neurostimulator 24A. As shown in FIG. 2, device 12 delivers neurostimulation therapy via electrodes 37A, 37B, 37C, 37D of lead 10 (collectively "electrodes"). Electrodes 37 may be ring electrodes arranged on an axial lead or pad electrodes arranged in an array on a paddle lead. The configuration, type and number of electrodes 37 illustrated in FIG. 2 are merely exemplary. Electrodes 37 are electrically coupled to a therapy delivery circuit 36 via lead 10.

Therapy delivery circuit 36 may, for example, include an implantable pulse generator coupled to a power supply 38 that generates stimulation energy from power delivered by a battery 40. The implantable pulse generator within therapy delivery circuit 36 delivers electrical pulses to patient 12 via at least some of electrodes 37 under the control of a processor 42. In one example, therapy delivery circuit 36 may deliver neurostimulation pulses with parameters selected to have values effective in controlling or managing symptoms of urinary incontinence, such as involuntary leakage. An exemplary range of neurostimulation stimulation pulse parameters likely to be effective in treating incontinence, e.g., when applied to the sacral or pudendal nerves, are as follows:

1. Frequency: from approximately 0.5 Hz to 500 Hz, in one embodiment from approximately 10 Hz to 250 Hz, and in yet another embodiment from approximately 10 Hz to 25 Hz.

2. Amplitude: from approximately 0.1 volts to 50 volts, in one embodiment from approximately 0.5 volts to 20 volts, and in yet another embodiment from approximately 1 volt to 10 volts.

3. Pulse Width: from about 10 microseconds to 5000 microseconds, in one embodiment from approximately 100 microseconds to 1000 microseconds, and in yet another embodiment from approximately 180 microseconds to 450 microseconds.

Processor 42 controls the implantable pulse generator within therapy delivery circuit 36 to deliver neurostimulation therapy according to selected stimulation parameters. Specifically, processor 42 controls therapy delivery circuit 36 to deliver electrical pulses with selected amplitudes, pulse widths, and rates specified by the programs. In addition, processor 42 also controls therapy delivery circuit 36 to deliver the neurostimulation pulses via selected subsets of electrodes 37 with selected polarities.

Processor 42 may control therapy delivery circuit 36 to deliver each pulse according to a different program, thereby interleaving programs to simultaneously treat different symptoms or provide a combined therapeutic effect. For example, in addition to treatment of urinary incontinence, neurostimulator 24A may be configured to deliver neurostimulation therapy to treat pain. Processor 42 may include a microprocessor, a controller, a digital signal processor (DSP), an application-specific integrated circuit (ASIC), an field-programmable gate array (FPGA), discrete logic circuitry, or the like.

Neurostimulator 24A also includes a memory 46. In some embodiments, memory 46 stores multiple sets of stimulation parameters that are available to be selected by patient 12 or a clinician for delivery of neurostimulation therapy. For example, memory 46 may store stimulation parameters transmitted by clinician programmer 34. Memory 46 also stores program instructions that, when executed by processor 42, cause device 12 to deliver neurostimulation therapy.

In the example of FIG. 2, memory 46 may store one or more trial programs 47 and one or more chronic programs 49 that control delivery of stimulation pulses for a trial mode and a chronic mode, respectively. In this case, an external device such as clinician programmer 34 or patient programmer 36 may send a signal to cause neurostimulator 24 to select either trial program 47 or chronic program 49, which are already loaded into memory 46. In other embodiments, trial and chronic programs may be selectively loaded into memory 46, e.g., by programming from clinician programmer 34 or patient programmer 36, to cause neurostimulator 24 to enter either the trial mode or the chronic mode.

Memory 46 may include any volatile, non-volatile, magnetic, optical, or electrical media, such as a RAM, ROM, CD-ROM, hard disk, removable magnetic disk, memory cards or sticks, NVRAM, EEPROM, flash memory, and the like. Accordingly, the invention also contemplates computer-readable media storing instructions to cause processor 42 to provide the functionality described herein.

A telemetry circuit 44 supports wireless communication between device 12, clinician programmer 34, patient programmer 36, or some combination thereof. In addition, in some embodiments, neurostimulator 24A may optionally include a timer 48 to be used during the trial mode. Timer 48 may serve to time the duration of the trial period, in some embodiments. For example, upon initiation of the trial period, timer 48 starts running to track the elapsed time in the trial period relative to a maximum trial period time. In some embodiments, when timer 48 expires, processor 42 responds by disabling therapy delivery circuit 36 to terminate the trial mode. In other words, processor 42 stops the trial period by stopping delivery of neurostimulation therapy to patient 12 by trial neurostimulator 24A.

In this manner, implantable neurostimulator 24A can be configured to prevent patient 12 or a physician from prolonging the trial period beyond a prescribed period of time. Rather, implantable neurostimulator 24A has a finite period of operation, determined by a maximum trial period that may be specified by the manufacturer or in a programmable manner by a clinician. In chronic mode, timer 48 may be used in some embodiments to serve as a method to ensure clinician evaluation of stimulation throughout chronic therapy. In other words, the chronic mode may be periodically disabled, e.g., with advance warning to the patient through patient programmer 36, to compel a clinical visit by the patient for periodic evaluation. Timer 48 may be implemented in hardware using a real-time clock, in software by processor 42, or a combination thereof. Accordingly, timer 48 is illustrated as a separate component in FIG. 2 merely for exemplary purposes.

Battery 40 of implantable neurostimulator 24A may be selected based on the stimulation therapy needed. In some cases, battery 40 may be a conventional lithium battery normally used in typical stimulation devices. The size and shape of battery 40 may be different to make implantable stimulator 24 smaller to fit in certain places on the patient or to allow a plurality of stimulation or sensing leads to be attached. In some embodiments, other battery technologies such as Nickel-metal-hydride or NiCad may be used in battery 40.

Figure 3:
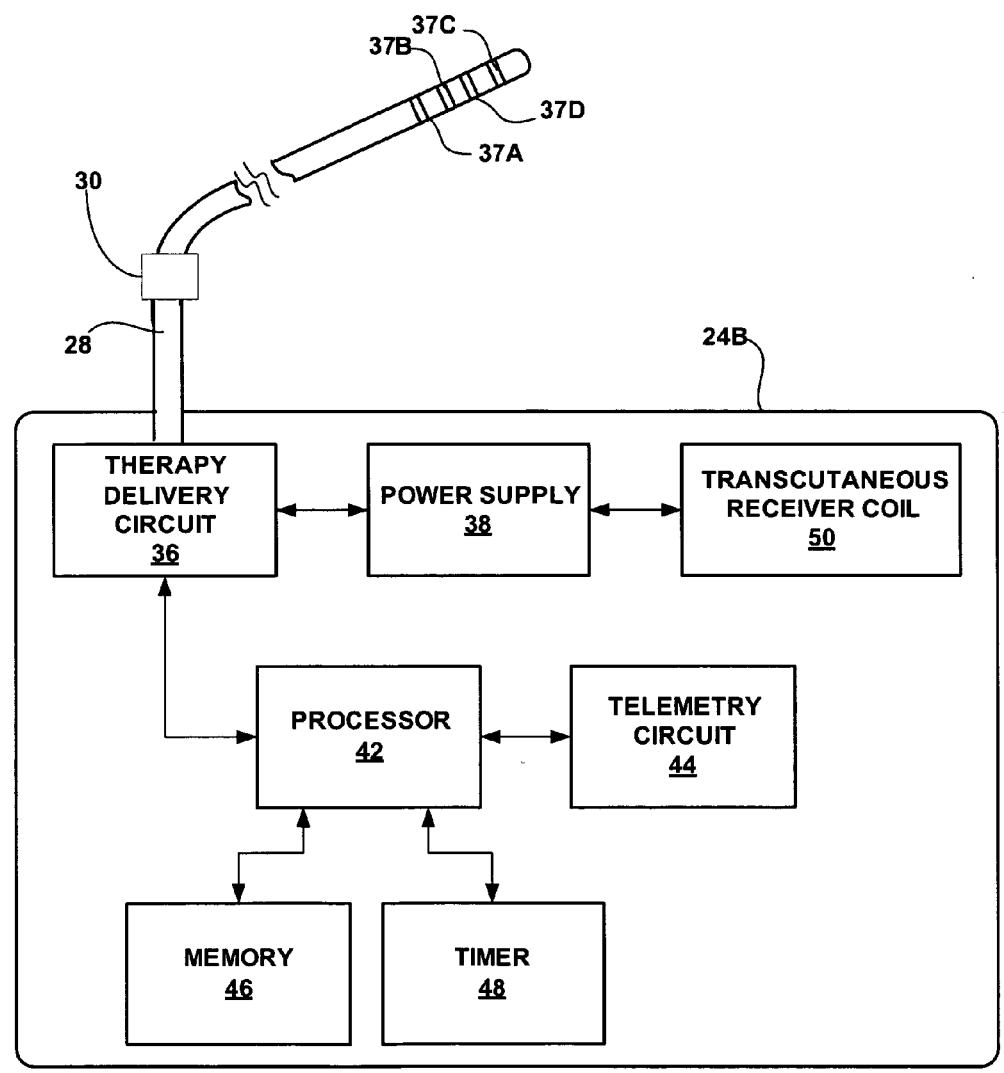
FIG. 3 is a block diagram illustrating various components of another implantable neurostimulator.

FIG. 3 is a block diagram illustrating various components of another implantable neurostimulator 24B. Neurostimulator 24B conforms substantially to neurostimulator 24A, but incorporates a transcutaneous receiver coil 50 instead of a battery 40. Transcutaneous receiver coil 50 is implanted with neurostimulator 24B and transduces electromagnetic energy received from an external coil into power for power supply 38. In this embodiment, neurostimulator 24B does not rely on battery resources as a power supply. Instead, neurostimulator 24B receives power via transcutaneous receiver coil 50 and controls the duration of the trial period and any subsequent chronic period in response to timer 48.

Figure 4:
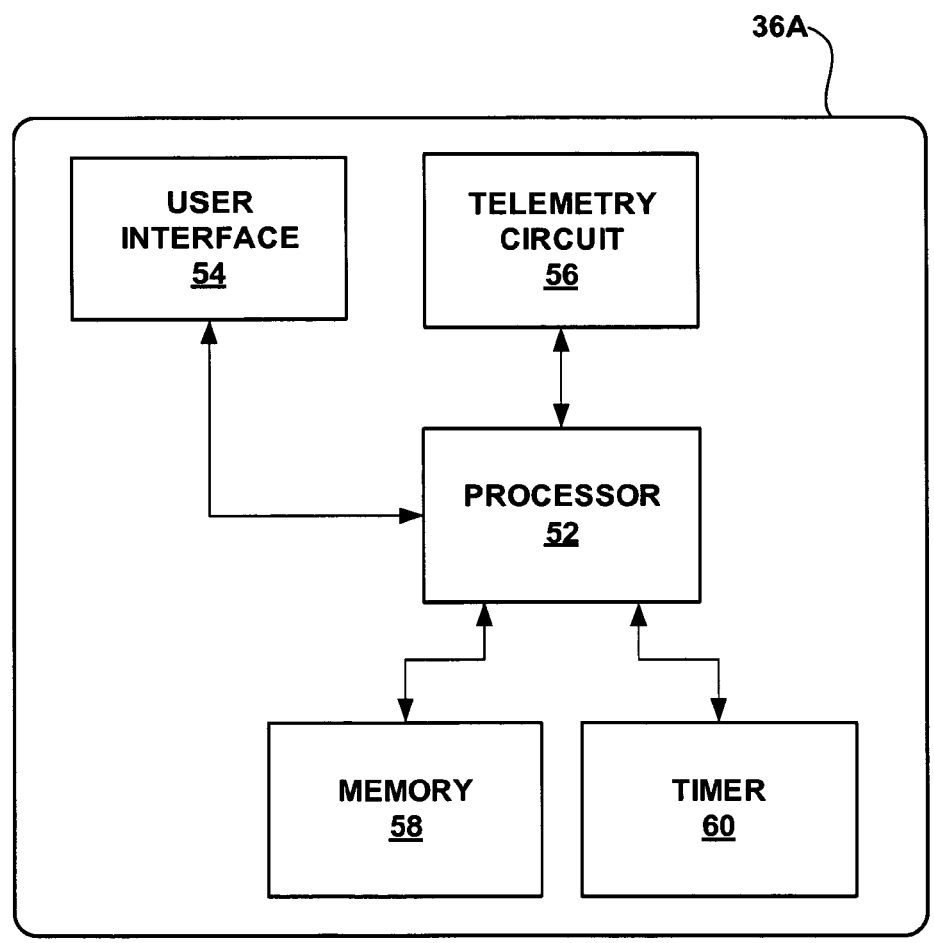
FIG. 4 is a block diagram illustrating various components of a patient programmer for use with the implantable neurostimulation system of FIG. 1.

FIG. 4 is a block diagram illustrating various components of a patient programmer 36A for use with one embodiment of the implantable neurostimulation system 20 of FIG. 1. As shown in FIG. 4, patient programmer 36A includes a processor 52, a user interface 54, and a telemetry circuit 56 for communication with telemetry circuit 44 of either of neurostimulators 24A, 24B, or clinician programmer 34. Patient programmer 36A also includes memory 58 to store parameters, settings and instructions, and optionally a timer 60 for use during the trial mode, the chronic mode, or both. Timer 60 may be implemented in hardware or software, and may operate as a programmable feature of processor 52.

Patient programmer 36A responds to user input entered via user interface 54 to adjust stimulation parameters, settings, and the like. The scope of adjustments permitted by patient programmer 36A may vary according to whether neurostimulator 24 is in trial mode or chronic mode. In addition, patient programmer 36A may interrogate neurostimulator 24 to obtain parameters, settings, and other operational data. For example, patient programmer 36A may be used to initially program neurostimulator 24 for the trial period, and to upload parameters, settings, and other operational data from neurostimulator 24 upon expiration of the trial period. During the course of the trial period or chronic period, neurostimulator 24 may store a variety of information concerning adjustments made by the user, usage profiles and the like.

Notably, patient programmer 36A is physically decoupled from neurostimulator 24 in the sense that neurostimulator 24 is implanted and the patient programmer is external to patient 12. While patient programmer 36A may be used during trial mode, chronic mode, or both, some embodiments of patient programmer 36A may include separate patient programmers for use during trial mode and chronic mode. This distinction may make it possible to save cost on the trial programmer, which may be less durable and contain fewer features than the full chronic programmer. Accordingly, patient programmer 36A may upload applicable parameters, settings, and operational information from neurostimulator 24 at the end of the trial period, and then transfer that information directly to chronic programmer, providing significant convenience to the physician and patient.

Patient programmer 36A may operate with a rechargeable or replaceable battery (not shown). In the example of FIG. 4, it is assumed that neurostimulator 24 includes its own battery. In other embodiments, as described herein, patient programmer 36A may deliver power to neurostimulator 24 transcutaneously. In addition, rather than download operational parameters and settings to neurostimulator 24 for substantially independent operation by the neurostimulator, patient programmer 36A may dynamically control the operation of the neurostimulator by continuous communication with the neurostimulator via telemetry circuit 44.

In addition, in some embodiments, patient programmer 36A, rather than neurostimulator 24, may control the end of the trial period. For example, processor 52 may be responsive to expiration of a finite period of time, as indicated by timer 60. In this case, processor 52 transmits a signal to implanted neurostimulator 24 instructing the neurostimulator to cease operation. After the clinician analyzes the efficacy and safety of the stimulation therapy during the trial period, patient programmer 36A may be used to renew a subscription for neurostimulator 24 and enable it to function in chronic mode for an unlimited time period, subject to longevity of battery resources in battery-powered systems. In some embodiments, the chronic mode may necessitate a fee or other action or commitment before the subscription to support chronic mode is activated.

Alternatively, processor 52 may simply terminate communication with neurostimulator 24 at the end of the trial period, in which case the neurostimulator terminates operation. Accordingly, termination of the trial period may be initiated within neurostimulator 24 or within patient programmer 36A, and may be accomplished in a variety of ways.

Figure 5:
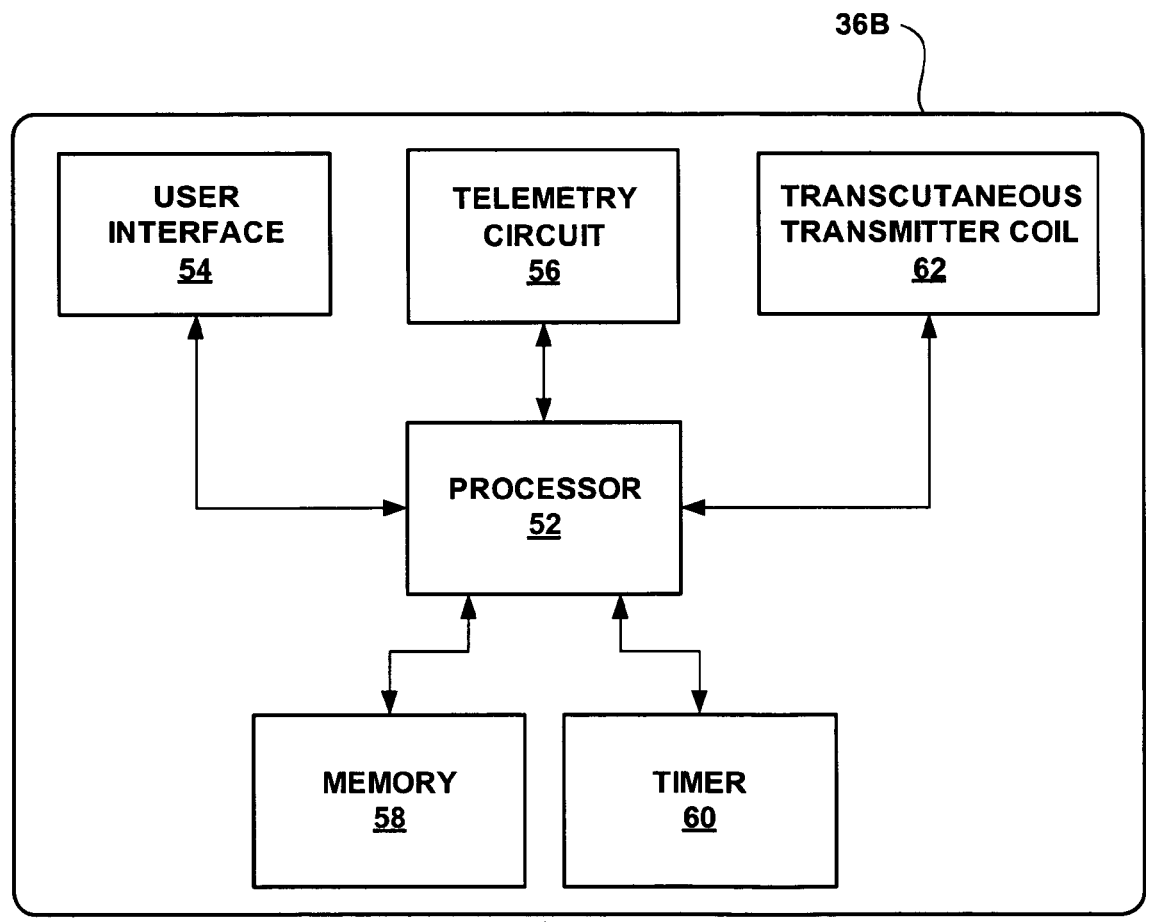
FIG. 5 is a block diagram illustrating various components of another patient programmer for use with the implantable neurostimulation system of FIG. 1.

FIG. 5 is a block diagram illustrating various components of another patient programmer 36B for use with the implantable neurostimulation system 20 of FIG. 1. Patient programmer 36B conforms substantially to patient programmer 36A of FIG. 4. However, patient programmer 36B further includes a transcutaneous transmitter coil 62 to deliver electromagnetic energy to transcutaneous receiver coil 50 of neurostimulator 24B for transformation into operating power.

Accordingly, patient programmer 36B is worn by the patient. Patient programmer 36B, or at least transcutaneous transmitter coil 62, is positioned adjacent neurostimulator 24 to provide effective electromagnetic coupling between the transcutaneous transmitter coil and transcutaneous receiver coil 50. In the example of FIG. 5, termination of the trial mode can be made by simply terminating the supply of power from transcutaneous transmitter coil 62 and transcutaneous receiver coil 50. In chronic mode, electromagnetic coupling should not be terminated. However, if this occurs, the renewed subscription is not invalidated. Once neurostimulator 24 receives power again, chronic mode may continue once again without interruption.

Figure 6:
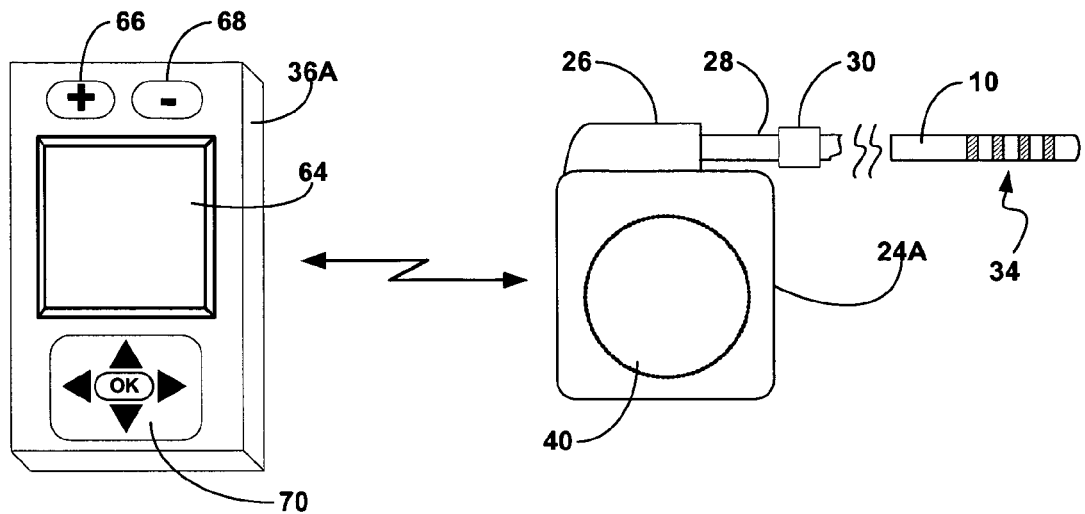
FIG. 6 is a diagram of a patient programmer and an implantable neurostimulator with a battery as a power source.

FIG. 6 is a diagram of an implantable trial neurostimulator 24A with a small battery 40 as a power source. In the example of FIG. 6, battery 40 is depicted as a coin cell battery, although other battery configurations may be used. In general, battery 40 may have a power capacity and longevity of several years, similar to batteries used in other commercially available neurostimulators.

FIG. 6 also depicts patient programmer 36A. As shown in FIG. 6, patient programmer 24A may include buttons 66, 68 to increase and decrease stimulation settings, respectively. In addition, patient programmer 36A includes a display 64, and navigational buttons 70 to permit navigation and selection of control options presented via the display. Buttons 66, 68, 70 and display 64 form part of user interface 54. In some cases, display 64 may present information advising patient 12 that expiration of the trial period is approaching. This information may help a patient receiving positive therapy by limiting the time between the end of the trial period and the start of the chronic period.

Figure 7:
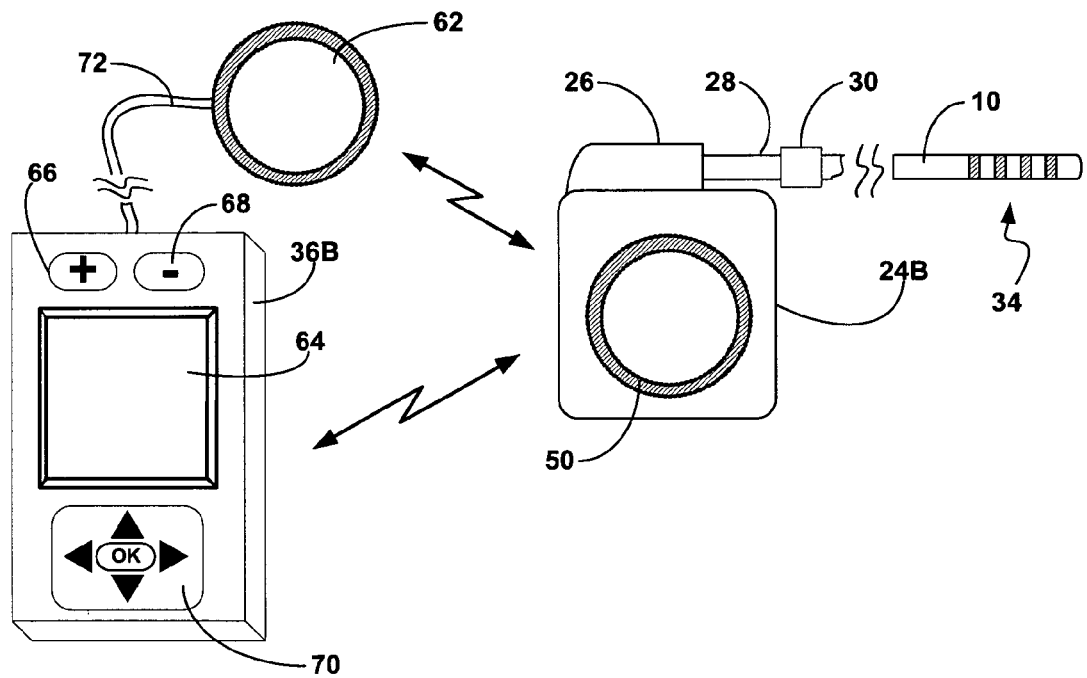
FIG. 7 is a diagram of a patient programmer and an implantable neurostimulator with a transcutaneous receiver coil interface for power delivery.

FIG. 7 is a diagram of an implantable neurostimulator 24B with a transcutaneous receiver coil 50 for power delivery. In particular, patient programmer 36B includes a transcutaneous receiver coil 50, which either resides within or extends from a housing associated with neurostimulator 24B. Transcutaneous receiver coil 50 receives electromagnetic energy from transcutaneous transmitter coil 62, which may be integrated with patient programmer 36B or extend from a cable 72, as shown in FIG. 7. With the exception of transcutaneous transmitter coil 62, patient programmer 36B may otherwise conform to patient programmer 36A of FIG. 6.

Figure 8:
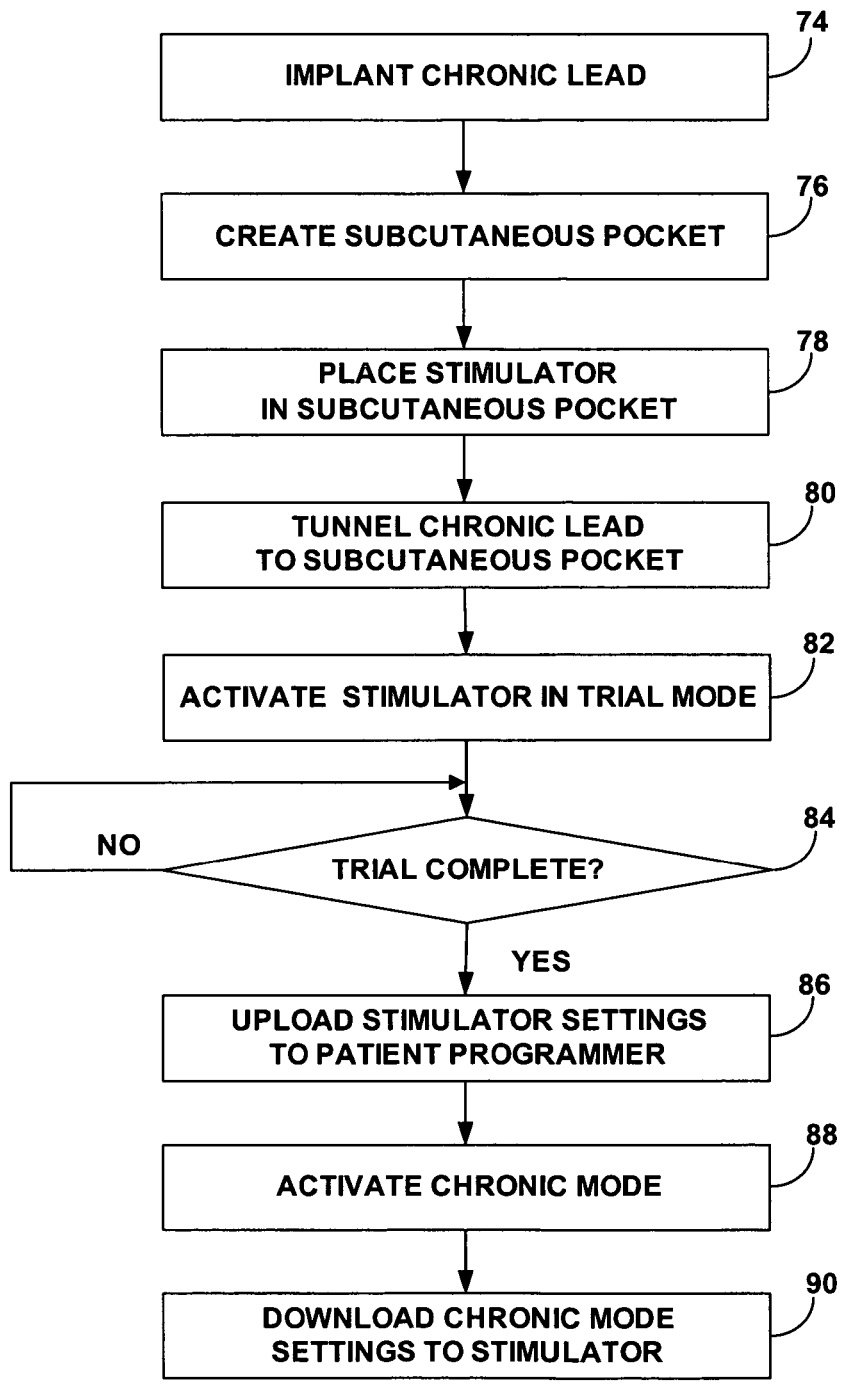
FIG. 8 is a flow diagram illustrating implantation and use of an implantable neurostimulator system in a trial mode and a chronic mode.

FIG. 8 is a flow diagram illustrating implantation and use of an implantable neurostimulator system 20 in accordance with the invention. As shown in FIG. 8, a chronic stimulation lead 10 is first implanted (74), e.g., as shown in FIG. 1. In some embodiments, lead 10 could be chronic or temporary. With neurostimulator 24 implanted in the chronic implant site, however, it may be desirable to use the chronic lead and thereby avoid the need to withdraw a temporary lead and replace it with the chronic lead after a successful trial period.

Upon surgical creation of a subcutaneous pocket (76), the neurostimulator is placed in the subcutaneous pocket for implantation (78). The chronic lead is subcutaneously tunneled through the body of patient 12 to the subcutaneous pocket (80). As shown in FIG. 1, for example, the lead may extend from sacrum 16 to a subcutaneous pocket 31 in the upper left buttock area of patient 12.

When lead 10 is tunneled to subcutaneous pocket 31, the lead is connected to neurostimulator 24 either directly or via a lead extension and connector. Before connecting lead 10 to neurostimulator 24, and tunneling the lead, a test stimulator may be connected to the lead to deliver neurostimulation for assistance in determining lead placement, lead depth and electrode selection.

Once the subcutaneous pocket 31 is sealed, neurostimulator 24 is activated for use in trial mode for the duration of the trial period (82). Patient 12 thereafter goes about his daily routine, and may control neurostimulator 24 via patient programmer 36. When the trial period is complete (84), e.g., as evidenced by expiration of a timer within trial neurostimulator 24 or patient programmer 36, the neurostimulator ceases operation.

Patient programmer 36, or physician programmer 34, then may upload from neurostimulator 24 a set of neurostimulator parameters, settings, operational information or the like either pre-programmed or accumulated during the course of the trial period (86). The information can be uploaded to patient programmer 36.

If the results are unfavorable and stimulation is unsuccessful to treat the condition of the patient, neurostimulator 24 and lead 10 may be removed from the patient. If the results of the trial period are favorable, the physician may activate the chronic mode of neurostimulator 24 for operation in chronic mode (88). Following the reactivation of neurostimulator 24 in chronic mode, patient programmer 36 or physician programmer 34 may be used to download at least some updated parameters, settings, and other operational information to modify stimulation therapy based upon information received from the trial period (90). In this manner, patient programmer 36 or physician programmer 34 can be used to quickly and conveniently program the chronic mode based on the results of the trial period. This feature can greatly simplify programming for the chronic period following the trial period.

In other embodiments, instead of or, in addition to, authorizing transition from the trial mode to the chronic mode, authorization may serve to unlock additional features of the implanted stimulator. As examples, a clinician or administrator, or a manufacturer of the implanted stimulator, may provide an authorization to activate features such as a voiding diary, different algorithms, different stimulation patterns and the like. The authorization could be provided to any element within the neurostimulation system, such as a physician programmer, patient programmer or the implanted stimulator. The authorization may be an authorization key or code that is obtained from a clinician or a manufacturer of the neurostimulator.

In some cases, the authorization may be downloaded or otherwise obtained from a manufacturer for an additional fee, somewhat like a software license. The authorization may be obtained on a recurring basis, for a recurring fee, to permit extended use of the neurostimulator or particular features of the neurostimulator. For example, an initial payment and authorization may support use of the neurostimulator or particular features of the neurostimulator for a period of time, e.g., one year. After a year of use, the neurostimulator or features "expire" in the sense that they are deactivated. Upon payment of a renewal fee, the neurostimulator or features are reactivated, providing another "subscription" period for the user.

As a further variation, in the case of a rechargeable neurostimulator that is recharged at periodic intervals, a fee could be charged each time the battery in the neurostimulator is recharged. If the fee is not paid, the neurostimulator is inactivated.

In each of the renewable scenarios, features can be extended or unlocked on a selective basis, providing a pay as you go approach for patients and the ability to select appropriate features on an a la carte basis.

Many embodiments of the invention have been described. Various modifications may be made without departing from the scope of the claims. These and other embodiments are within the scope of the following claims.

The invention claimed is:

1. An implantable neurostimulator comprising:
a neurostimulation generator;
a processor that controls the neurostimulation generator to generate neurostimulation in a trial mode as a first operating mode upon initial implantation of the neurostimulator and before generation of electrical stimulation in any chronic mode by the neurostimulation generator, to evaluate efficacy of the neurostimulator; and
one or more sensors that sense one or more parameters related to a patient during the trial mode,
wherein the processor controls the neurostimulation generator to generate neurostimulation in the chronic mode after completion of the trial mode and only if the trial mode indicates that the neurostimulator provides efficacious therapy to the patient, wherein the processor controls the neurostimulation generator to generate neurostimulation in the chronic mode according to a set of electrical stimulation parameter values that is different than any sets of electrical stimulation parameter values that define neurostimulation generated during the trial mode.

2. The implantable neurostimulator of claim 1, wherein the processor is configured to operate the neurostimulator in the trial mode for a period of less than six months, and is configured to operate the neurostimulator in the chronic mode for a period of more than six months.

3. The implantable neurostimulator of claim 1, wherein the one or more parameters related to the patient comprise bladder pressure, bladder contractile force, urinary sphincter pressure, urine flow rate, urine flow pressure, voiding amount, urine flow velocity, urine temperature, bladder temperature, impedance, urinary pH, or chemical constituency of the urine.

4. The implantable neurostimulator of claim 1, wherein the one or more parameters related to the patient comprise cardiac activity, respiratory activity, electromyographic activity, a posture or activity level of the patient.

5. The implantable neurostimulator of claim 1, wherein the processor is configured to activate the trial mode in response to a first signal generated by an external programmer and terminate the trial mode in response to a second signal generated by the external programmer.

6. The implantable neurostimulator of claim 1, wherein the processor is configured to activate the trial mode in response to a first signal generated by an external programmer and terminate the trial mode in response to a second signal generated by the implanted neurostimulator.

7. The implantable neurostimulator of claim 1, wherein the processor is configured to control the one or more sensors to sense one or more patient parameters during the chronic mode.

8. The implantable neurostimulator of claim 7, wherein the one or more patient parameters comprise bladder pressure, bladder contractile force, urinary sphincter pressure, urine flow rate, urine flow pressure, voiding amount, urine flow velocity, urine or bladder temperature, impedance, urinary pH, or chemical constituency of the urine.

9. The implantable neurostimulator of claim 7, wherein the one or more patient parameters comprise cardiac activity, respiratory activity, electromyographic activity, posture or activity level of the patient.

10. The implantable neurostimulator of claim 7, wherein the processor is configured to control the one or more sensors to sense one or more patient parameters in the trial mode that are different than the one or more parameters related to the patient sensed during the chronic mode.

11. The implantable neurostimulator of claim 7, wherein the processor is configured to control the one or more sensors to sense one or more patient parameters in the trial mode at a different frequency than the one or more parameters sensed in the chronic mode.

12. The implantable neurostimulator of claim 2, wherein the period includes a plurality of days.

13. The implantable neurostimulator of claim 1, wherein the processor is configured to permit a greater scope of stimulation parameter adjustments by the patient in the chronic mode than in the trial mode.

14. The implantable neurostimulator of claim 1, wherein the neurostimulator includes a lead carrying one or more electrodes for delivery of stimulation pulses, and wherein the neurostimulator is configured to apply neurostimulation for treatment of incontinence, a gastric mobility disorder, pain relief, sexual dysfunction, or interstitial cystitis.

15. The implantable neurostimulator of claim 1, wherein the processor terminates the trial mode upon expiration of a maximum trial period of time.

16. The implantable neurostimulator of claim 1, wherein the processor is configured to unlock one or more features of the neurostimulation generator in the chronic mode not available in the trial mode.

17. The implantable neurostimulator of claim 16, wherein the one or more features comprise at least one of a voiding diary, a different algorithm, or a different stimulation pattern.

18. The implantable neurostimulator of claim 17, wherein the one or more features comprise a different stimulation pattern.

19. An implantable neurostimulator comprising:
a pulse generator;
one or more sensors configured to sense one or more parameters related to a patient;
a memory storing a trial mode program and a chronic mode program that is different than the trial mode program; and
a processor that controls the pulse generator to apply stimulation pulses according to the trial mode program in a first operating mode upon initial implantation of the neurostimulator to evaluate efficacy of the neurostimulator, wherein the first operating mode occurs prior to operation of the neurostimulator in any chronic mode, and apply stimulation pulses according to the chronic mode program as a second mode after completion of the trial mode only if the trial mode indicates that the neurostimulator provides efficacious therapy to the patient, wherein the chronic mode program is different than any sets of electrical stimulation parameter values that define stimulation applied during the trial mode, and controls the one or more sensors to sense one or more patient parameters during the trial mode.

20. The implantable neurostimulator according to claim 19, wherein the processor also controls the one or more sensors during the chronic mode.

21. The implantable neurostimulator according to claim 20, wherein the one or more sensors are controlled differently by the processor during the trial mode and the chronic mode.

22. The implantable neurostimulator of claim 19, wherein the processor terminates the delivery of stimulation according to the trial mode program upon expiration of a maximum trial period of time.

23. An implantable electrical stimulator comprising:
an electrical stimulation generator;
a processor that controls the electrical stimulation generator to generate electrical stimulation in a trial mode as a first mode following implantation of the electrical stimulator and before generation of stimulation in any chronic mode; and
one or more sensors that sense one or more parameters related to a patient during the trial mode,
wherein the processor controls the electrical stimulation generator to generate electrical stimulation in the chronic mode after completion of the trial mode only if the trial mode indicates that the electrical stimulator provides efficacious therapy to the patient, and controls the electrical stimulation generator to generate no electrical stimulation in any chronic mode prior to the generation of electrical stimulation in the trial mode, and wherein the processor controls the electrical stimulation generator to generate electrical stimulation in the chronic mode according to a new program relative to programs that define neurostimulation generated during the trial mode, and
wherein the processor controls the electrical stimulation generator to operate in the trial mode for a trial period, and controls the electrical stimulation generator to stop operating after the trial period until authorization to continue operating is received.

24. The system implantable electrical stimulator of claim 23, wherein the processor controls the electrical stimulation generator to stop generating stimulation according to the trial mode upon expiration of a maximum trial period of time.

25. The implantable electrical stimulator of claim 23, wherein the trial period is prescribed.

26. An implantable neurostimulator comprising:
an electrical stimulation generator; and
a processor that controls the electrical stimulation generator to generate neurostimulation in a trial mode as a first operating mode upon initial implantation of the neurostimulator to evaluate efficacy of the neurostimulator and controls the neurostimulation generator to generate neurostimulation in a chronic mode according to a new program relative to programs that define neurostimulation generated during the trial mode, wherein the processor controls the neurostimulation generator to generate neurostimulation in the chronic mode after completion of the trial mode and only if the trial mode indicates that the neurostimulator provides efficacious therapy to the patient, and wherein the processor controls the electrical stimulation generator to operate in the trial mode for a trial period, and controls the electrical stimulation generator to stop operating after the trial period until authorization to continue operating is received.

\* \* \* \* \*